（12) United States Patent
Patel-Framroze

(10) Patent No.: US 11,352,311 B1
(45) Date of Patent: Jun. 7, 2022

(54) SINGLE-STEP STEREOSPECIFIC SYNTHESIS OF (S)-2-CHLOROPROPIONIC ACID ALKYL ESTER

(71) Applicant: Bomi Patel-Framroze, Portola Valley, CA (US)

(72) Inventor: Bomi Patel-Framroze, Portola Valley, CA (US)

( * ) Notice: Subject to any disclaimer, the term of this patent is extended or adjusted under 35 U.S.C. 154(b) by 0 days.

(21) Appl. No.: 17/359,592

(22) Filed: Jun. 27, 2021

(51) Int. Cl.
*C07C 67/307* (2006.01)
(52) U.S. Cl.
CPC .................................. *C07C 67/307* (2013.01)
(58) Field of Classification Search
None
See application file for complete search history.

(56) References Cited

U.S. PATENT DOCUMENTS 4,334,083 A * 6/1982 Buathier ............... C07C 67/307
560/150
4,408,068 A * 10/1983 Koch .................... C07C 301/00
560/226

FOREIGN PATENT DOCUMENTS

| CN | 101348432 | * | 1/2009 |
| EP | 0179603 | * | 4/1986 |
| EP | 0257716 | * | 3/1988 |
| FR | 1479271 | * | 5/1967 |
| GB | 2055802 | * | 3/1981 |

OTHER PUBLICATIONS

Frankland ("CVI. The action of thionyl chloride on lactic acid and on ethyl lactate" J. Chem. Soc., vol. 105, 1914, p. 1101-1115). (Year: 1914).*
Gubicza ("Enzymatic esterification in ionic liquids integrated with pervaporation for water removal" Green Chemistry, 2003, vol. 5, p. 236-239) (Year: 2003).*
Meshram ("A green approach for efficient alpha-halogenation of beta-dicarbonyl compounds and cyclic ketones using N-halo succinimides in ionic liquids" Tetrahedron Letters, 47, 2006, p. 991-995) (Year: 2006).*
Violleau ("Optical methyl 2-chloropropionate synthesis by decomposition of methyl 2-(chlorocarbonyloxy)propionate with hexaalkylguanidinium chloride hydrochloride" Tetrahedron, 2002(58), p. 8607-8612) (Year: 2002).*

* cited by examiner

*Primary Examiner* — Amy C Bonaparte

(57) ABSTRACT

Provided herein is a process to react optically pure alkyl lactates with thionyl chloride in the presence of a catalytic amount of a lewis base ionic liquid to produce optically pure chloropropionic acid alkyl esters.

7 Claims, No Drawings

SINGLE-STEP STEREOSPECIFIC SYNTHESIS OF (S)-2-CHLOROPROPIONIC ACID ALKYL ESTER

FIELD

The present disclosure relates to a new one-pot, stereospecific, process for the manufacture of (S)-2-chloropropionic acid alkyl ester starting from (L)-alkyl lactate using stoichiometric thionyl chloride and catalytic lewis base ionic liquid resulting in high overall yield with no epimerization and no ester hydrolysis.

BACKGROUND (S)-2-chloropropionic acid methyl ester is a potential intermediate compound in the manufacture of the agrochemical phenoxy herbicide, mecoprop-p, which is the active (R)-enantiomer of the racemic herbicide mecoprop, 2-(4-chloro-2-methylphenoxy)propanoic acid.

A direct preparation of ethyl 2-chloropro-pionate by chlorinating ethyl lactate with thionyl chloride was first described by Frankland and Garner in J. Chem. Soc. (1914) v105, 1101-1115 in a two stage process. The first stage is the reaction of ethyl lactate with thionyl chloride to form a chlorosulphinate and the second stage is the thermal decomposition of the chlorosulphinate obtained above, by heating in the presence of pyridine hydrochloride as a catalyst, to give the desired ethyl 2-chloropropionate. This reference presented numerous difficulties: Firstly, there is vigorous uncontrolled evolution of HCl gas which is not amenable to industrial production due to safety concerns. Secondly, various side reactions occurred leading to the formation of undesirable byproducts which require distillation for purification which lowers the yield of the desired ethyl 2-chloropropionate. Thirdly, when applied to an isomerically pure starting material, (R) or (S)-ethyl lactate, the use of pyridine hydro-chloride as a catalyst caused partial racemisation of the ethyl 2-chloropropionate to below 80% ee, rendering it unusable for the production of enantiomerically pure agrochemicals, such as (R)-2-(4-chloro-2-methylphenoxy)propionic acid in accordance with the process de-scribed in French Pat. No. 1,479,271.

In 1979 Rhone Poulenc published an improvement on the above process for making (S)-2-chloropropionic acid methyl ester from L-methyl lactate (U.S. Pat. No. 4,334,083). According to the inventors, in their process, the evolution of hydrogen chloride gas was better controlled, byproduct production was reduced and racemization of the resultant (R) or (S)-2-chloropropionic acid methyl ester when starting with (S) or (R) methyl lactate respectively, was minimized. This was achieved by: (a). gradually adding a mixture of methyl lactate in thionyl chloride to a mixture of thionyl chloride and pyridine or dimethylformamide (organic base); (b). Using a small amount of pyridine (between 0.1 and 1.0 percent by weight) to minimize racemization; (c). using a temperature between 15 to 65° C. during the first stage (d). carrying out a slow addition (3 to 5) hours to add the thionyl chloride in the first stage; (e). using a lower temperature of less than 80° C. and a long total time of 4 to 10 hours in stage two.

Although this process improved on Frankland and Garner's earlier process, it had long reaction times, inconsistent racemization, and required distillation and its commercial utility was eclipsed by the use of enzymes to stereospecifically resolving racemic mixtures of 2-chloropropionic acid as described in EP0179603 and EP0257716 (1988) to give the desired (S)-2-chloropropionic acid and recycling the (R) acid isomer by epimerization to the racemic mixture for further resolution. However, the enzymatic process used commercially today, is multi-stepped with recycles of starting material required, is energy inefficient and requires large volume dilutions that are not consistent with environmentally sensitive green manufacture.

Consequently, there still exists a need to produce (S)-2-chloropropionic acid methyl ester, in high epimeric excess (ee) using a single step reaction, in a high yield and purity which does not require distillation, that has a low environmental impact and uses no solvents, for use as an intermediate in the production of agrochemicals.

BRIEF SUMMARY

The present invention describes a rapid, single step reaction of L-methyl lactate and thionyl chloride in the presence of a catalytic quantity of a lewis base ionic liquid.

In some embodiments, the lewis base ionic liquid is 1,1,3,3-tetramethylguanidinium acetate.

In some aspects, the reaction can be carried out by reacting one molar equivalent of thionyl chloride and L-methyl lactate in the presence of 0.1-1.0 percent, weight to weight of L-methyl lactate, of the lewis base ionic liquid, 1,1,3,3-tetramethylguanidinium acetate.

In some aspects, the total reaction is completed within 2 hours while still maintaining a controlled evolution of hydrochloric acid and sulfur dioxide.

In some aspects, the resultant (S)-chloropropionic acid methyl lactate requires no additional purification or fractional distillation prior to use as an intermediate in the production of (R)-2-(4-chloro-2-methylphenoxy)propionic (also known as mecoprop-p) herbicide.

DETAILED DESCRIPTION

Before describing the present invention in detail, it is to be understood that the terminology used herein is for the purpose of describing particular embodiments only, and is not intended to be limiting.

In accordance with the present invention, there is provided a process to produce the agrochemical intermediate (S)-2-chloropropionic acid methyl ester, in a highly stereospecific and cost effective manner, with high yields, with no solvent used, with no purification required and no recycle of starting materials.

Thus the method described herein uses the hitherto unknown use of 1,1,3,3-tetramethyl guanidinium acetate as a catalyst for the chlorination of 95 percent enantiomeric excess (ee) L-methyl lactate with a stoichiometric amount of thionyl chloride at 90° C. to form the desired (S)-chloropropionic acid methyl ester in 95 percent ee and 99 percent yield as shown in Example 1. As can be further seen in Example 2 and 3 below, a simple substitution of the lewis base ionic liquid with the previously described organic bases, pyridine or dimethylformamide, does not result in an equivalent result in optical nor GC purity. The broad claim of using lewis base ionic liquids is demonstrated by the use of two other lewis base ionic liquids as the catalyst, 1,1,3,3-tetramethylguanidinium tetrafluoroborate and 1,3-dimethyl-2-imidazolidinone tetrafluoroborate as seen in Examples 4 and 5 below respectively which resulted in similarly high optical and GC purity of (S)-2-chloropropionic acid methyl ester, as shown in Example 1.

This new method eliminates: (i) the hydrolysis of L-methyl lactate that could result in byproducts that would require purification; (ii) the use of any solvent requiring distillation; (iii) the need for low temperatures to control the reaction allowing for 5× faster reaction times; (iv) any loss of optical purity that requires fractional distillation purification before further use, as described in the prior art (U.S. Pat. No. 4,334,083).

It will be clear to those skilled in the art that modifications can be made to the process described herein without departing from the inventive concept set forth in our claims below.

Example 1

118 grams (1 mole) of thionyl chloride was charged into a 500 ml reactor pre-cooled to 15 to 20° C. To this was added 104 grams (1.0 mole) of 96.4% ee L-methyl lactate (no solvent $[alpha]_D^{20}=)+7.69°$ containing 0.230 grams (0.002 moles) of 1,1,3,3-tetramethylguanidinium acetate over 1 hour with slow agitation. After the addition is complete the reaction is heated to 90° C. and held at 90° C. for 1 hour. The reaction is cooled to room temperature and the resultant pale yellow oil (b.p.=132-133° C.) has 95.1% ee optical purity (S)-2-chloropropionic acid methyl ester (no solvent $[alpha]_D^{20}=)-24.81°$ and 98.8% yield, by GC area percent.

Example 2

130 grams (1.1 mole) of thionyl chloride was charged into a 500 ml reactor pre-cooled to 15 to 20° C. To this was added 104 grams (1.0 mole) of 95.0% ee L-methyl lactate containing 0.50 grams (0.5% of L-methyl lactate weight) of pyridine over 1 hour with slow agitation. After the addition is complete the reaction is heated to 90° C. and held at 90° C. for 1 hour. The reaction is cooled to room temperature and the resultant pale yellow oil (b.p.=132-133° C.) is 71.3% ee optical purity (S)-2-chloropropionic acid methyl ester using the same method as in Example 1 and 81.5% yield, by GC area percent with multiple impurity peaks.

Example 3

130 grams (1.1 mole) of thionyl chloride was charged into a 500 ml reactor pre-cooled to 15 to 20° C. To this was added 104 grams (1.0 mole) of 95.0% ee L-methyl lactate containing 1.0 grams (1% of L-methyl lactate weight) of dimethylformamide over 1 hour with slow agitation. After the addition is complete the reaction is heated to 90° C. and held at 90° C. for 1 hour. The reaction is cooled to room temperature and the resultant pale yellow oil (b.p.=132-133° C.) is 73.9% ee optical purity (S)-2-chloropropionic acid methyl ester using the same method as in Example 1 and 84.6% yield, by GC area percent with multiple impurity peaks.

Example 4

118 grams (1 mole) of thionyl chloride was charged into a 500 ml reactor pre-cooled to 15 to 20° C. To this was added 104 grams (1.0 mole) of 95.0% ee L-methyl lactate containing 0.804 grams (0.004 moles) of 1,1,3,3-tetramethylguanidinium tetrafluoroborate over 1 hour with slow agitation. After the addition is complete the reaction is heated to 90° C. and held at 90° C. for 1 hour. The reaction is cooled to room temperature and the resultant pale yellow oil (b.p.=132-133° C.) is 94.5% ee optical purity (S)-2-chloropropionic acid methyl ester using the same method as in Example 1 and 98.3% yield, by GC area percent.

Example 5

118 grams (1 mole) of thionyl chloride was charged into a 500 ml reactor pre-cooled to 15 to 20° C. To this was added 104 grams (1.0 mole) of 95.0% ee L-methyl lactate containing 0.201 grams (0.001 moles) of 1,3-dimethyl-2-imidazolidinone tetrafluoroborate over 1 hour with slow agitation. After the addition is complete, the reaction is heated to 90° C. and held at 90° C. for 1 hour. The reaction is cooled to room temperature and the resultant pale yellow oil (b.p.=132-133° C.) is 92.7% ee optical purity (S)-2-chloropropionic acid methyl ester using the same method as in Example 1 and 99.0% yield, by GC area percent.

What is claimed is:

1. A process that reacts an optically active alkyl lactate with thionyl chloride in the presence of a catalytic quantity of a Lewis basic ionic liquid to yield an optically active 2-chloropropionic acid alkyl ester.

2. A process according to claim 1, wherein the Lewis basic ionic liquid is 1,1,3,3-tetramethylguanidinium acetate.

3. A process according to claim 1, wherein the Lewis basic ionic liquid is 1,1,3,3-tetramethylguanidinium tetrafluoroborate.

4. A process according to claim 1, wherein the Lewis basic ionic liquid is 1,3-dimethyl-2-imidazolidinone tetrafluoroborate.

5. A process according to claim 1, wherein the alkyl lactate and thionyl chloride are reacted in equimolar quantities.

6. A process according to claim 1, wherein the Lewis basic ionic liquid concentration in the reaction is between 0.01 and 1.0 mole percent of the alkyl lactate.

7. A process according to claim 1, wherein the reaction temperature is between 80° C. and 90° C.

* * * * *